United States Patent [19]

Itatani et al.

[11] 4,294,976
[45] Oct. 13, 1981

[54] PROCESS FOR PRODUCING BIPHENYL COMPOUNDS

[75] Inventors: Hiroshi Itatani, Chiba; Hataaki Yoshimoto, Ichihara; Akinori Shiotani, Ichihara; Akiyoshi Yokota, Ichihara; Motozoh Yoshikiyo, Ichihara, all of Japan

[73] Assignee: UBE Industries, Ltd., Ube, Japan

[21] Appl. No.: 71,089

[22] Filed: Aug. 31, 1979

[30] Foreign Application Priority Data

Sep. 5, 1978 [JP] Japan ................................ 53/108097

[51] Int. Cl.³ .................... C07C 69/76; C07C 179/02; C07C 15/14
[52] U.S. Cl. ....................................... 560/76; 560/96; 568/609; 568/931; 570/182; 570/183; 570/127; 570/129; 585/425
[58] Field of Search ................... 560/76, 96; 568/609, 568/931; 570/182, 183, 127, 129; 585/425

[56] References Cited

U.S. PATENT DOCUMENTS 3,340,293 9/1967 Sharp et al. .......................... 560/76
3,895,055 7/1975 Itatani et al. ..................... 260/346.3
3,940,426 2/1976 Itatani et al. .

Primary Examiner—Paul J. Killos
Attorney, Agent, or Firm—Finnegan, Henderson, Farabow, Garrett & Dunner

[57] ABSTRACT

A biphenyl compound is produced from a corresponding aromatic monocyclic compound at a high yield thereof and a high percent selectivity thereto, by dehydrogenatively dimerizing the aromatic monocyclic compound with molecular oxygen in the presence of oxalic acid together with a organic palladium salt catalyst, under a pressure higher than the atmospheric pressure.

11 Claims, No Drawings

PROCESS FOR PRODUCING BIPHENYL COMPOUNDS

FIELD OF THE INVENTION

The present invention relates to a process for producing biphenyl compounds. More particularly, the present invention relates to a process for producing biphenyl compounds by dehydrogenatively dimerizing aromatic monocyclic compounds at a high percent selectivity to the biphenyl compounds.

BACKGROUND OF THE INVENTION

It is known that biphenyl compounds can be produced by various catalytic dehydrogenative dimerization of aromatic monocyclic compounds with molecular oxygen in the presence of a palladium-containing catalyst. However, it is also known that the conventional processes are disadvantageous in that the catalytic dehydrogenative dimerization results in production of a large amount of by-product having a high boiling point. This production of the by-product causes the yield of the resultant biphenyl compound and the percent selectivity to the biphenyl compound to become poor. Accordingly, it is desired to provide a new process for producing the biphenyl compounds from the aromatic monocyclic compounds at an excellent yield of the biphenyl compounds and percent selectivity to the biphenyl compounds.

SUMMARY OF THE INVENTION

An object of the present invention is to provide a process for producing a biphenyl compound at an increased yield thereof and percent selectivity thereto.

Another object of the present invention is to provide a process for producing a biphenyl compound accompanied by a reduced amount of by-product.

The above-mentioned objects can be attained by the process of the present invention, which comprises dehydrogenatively dimerizing an aromatic monocyclic compound with molecular oxygen in the presence of oxalic acid together with a catalyst comprising at least one organic palladium salt, under a pressurized condition, and; isolating the resultant biphenyl compound from the reaction mixture.

In the process of the present invention, it is important that the dehydrogenative dimerization reaction of the aromatic monocyclic compound be carried out in the presence of a combination of the organic palladium salt with the oxalic acid. This combination is highly effective for increasing the yield of the biphenyl compound and the percent selectivity to the biphenyl compound and for reducing the amount of the undesirable by-product.

DETAILED DESCRIPTION OF THE INVENTION

The aromatic monocyclic compound usable for the present invention is not limited to a special compound as long as the compound is capable of being dehydrogenatively dimerized. However, it is preferable that the aromatic monocyclic compound be selected from the group consisting of benzene and substituted benzene compounds having 1 to 4, more preferably, 1 to 2, substituents attached to the benzene ring thereof. The substituent on the benzene ring may be selected from the group consisting of unsubstituted and substituted alkyl radicals, having 1 to 5 carbon atoms, for example, unsubstituted or substituted methyl, ethyl, n-propyl, isopropyl, n-butyl, isobutyl and pentyl radicals; alkoxycarbonyl radicals having 1 to 5 carbon atoms, for instance, methoxycarbonyl, ethoxycarbonyl, propoxycarbonyl and butoxycarbonyl radicals; alkoxy radicals having 1 to 5 carbon atoms, for instance, methoxy, ethoxy, n-propoxy, isopropoxy and butoxy radicals; nitro radical and halogen atoms. The halogen atoms involve fluorine, chlorine and bromine atom. The above-mentioned substituted alkyl radicals may have one or more substituents selected from the group consisting of an acetyl radical and halogen atoms, for example, fluorine, chlorine and bromine atoms.

The substituted benzene compound usable for the present invention is preferably selected from the group consisting of toluene, o-, m- and p-xylenes, ethyl benzene, 1,2,4,-trimethyl benzene, o-chloromethyl benzene, methyl benzoate, butyl benzoate, dimethyl o-phthalate, dibutyl o-phthalate, dimethyl terephthalate, chlorobenzene, anisole, nitrobenzene, methyl toluylate, fluorobenzene, o-chlorotoluene, trifluorotoluene, 2,6-dimethylbenzyl acetate and xylylene diacetate.

The most preferable aromatic monocyclic compounds are benzene derivatives having 1 or 2 alkoxycarbonyl radicals each having 1 to 5 carbon atoms.

The catalyst usable for the present invention comprises at least one organic palladium salt. The organic palladium salt is not limited to a special compound as long as the palladium salt is of an organic acid. However, in order to produce the biphenyl compound at a high yield, it is preferable that the organic palladium salt be selected from the group consisting of palladium salts of aliphatic carboxylic acids, having 1 to 5 carbon atoms, for example, palladium formate, palladium acetate, palladium propionate, palladium butylate and palladium valerate. Also, the palladium salt may be selected from the group consisting of palladium salts of aromatic carboxylic acids, for example, palladium terephthalate and palladium benzoate. Moreover, the organic palladium salt may be palladium acetylacetonate. The most preferable palladium salt for the present invention is palladium acetate. In the process of the present invention, it is preferable that the organic palladium salt be used in an amount of from 0.01 to 100 millimoles, more preferably, from 0.05 to 5 millimoles, per mole of the aromatic monocyclic compound.

In the process of the present invention, it is essential that the dehydrogenative dimerization of the aromatic monocyclic compound be carried out in the presence of oxalic acid together with the organic palladium salt. The oxalic acid is preferably used in an amount of from 0.05 to 50 moles, more preferably, from 0.1 to 20 moles, per mole of the organic palladium salt. If the oxalic acid is used in an amount of more than 50 moles per mole of the organic palladium salt, the percent conversion of the aromatic monocyclic compound into the corresponding biphenyl compound might at time be poor. Also an amount of the oxalic acid smaller than 0.05 moles per mole of the organic palladium salt, might at times result in a poor percent selectivity to the resulting biphenyl compounds and, also, in a large yield of the by-product having a high boiling point. The dehydrogenative dimerization of the present invention may be carried out in the presence of a small amount of an organic additive together with the oxalic acid and the organic palladium salt. The additive may be selected from the group consisting of β-diketones, for example, acetylacetone, propionyl acetone, butyl acetone, benzoyl acetone, and; β-ketoesters, for instance, acetacetic esters and trifluoroacetacetic esters. The additive is used preferably in an amount of 4 moles or less, preferably, 2 moles or less, per mole of the organic palladium salt. The additive is effective for increasing the percent conversion of the aromatic monocyclic compound into the biphenyl compound.

In the process of the present invention, it is also essential that the dehydrogenative dimerization of the aromatic monocyclic compound be carried out by using molecular oxygen under a pressurized condition. If the pressurized condition is absent from the dehydrogenative dimerization, poor dehydrogenative dimerization will occur.

Preferably, the dehydrogenative dimerization is carried out under a pressure of from 4 to 400 kg/cm$^2$, more preferably, from 8 to 100 kg/cm$^2$. In this case, it is preferable that the molecular oxygen in the reaction mixture exhibit a partial pressure of at least 2 kg/cm$^2$, more preferably, 2 to 300 kg/cm$^2$, still more preferably, from 5 to 40 kg/cm$^2$. If the partial pressure of the molecular oxygen is less than 2 kg/cm$^2$, the organic palladium salt might at times deposit, as a palladium black, from the dehydrogenative dimerization reaction mixture.

The dehydrogenative dimerization reaction mixture may contain an inorganic additive consisting of at least one member selected from, for example, magnesium sulfate, sodium sulfate, activated alumina, silica gel, metallic aluminium, granulated metallic silicon. The above-mentioned inorganic additive may be slightly effective for increasing the percent selectivity to the biphenyl compound. However, it is not preferable that the dehydrogenative dimerization reaction mixture contain sodium acetate, lithium chloride and sulfuric acid, because these compounds cause the dehydrogenative dimerization reaction to be hindered.

Since the aromatic monocyclic compound usable for the process of the present invention is in the state of a liquid in the ambient atmosphere, it is not necessary to add a solvent to the reaction mixture. However, the reaction mixture may contain an inert solvent unless the solvent hinders the dehydrogenative dimerization reaction. Sometimes, a large amount of polar solvent, for example, dimethyl formamide, acetonitrile, water and acetone, in the reaction mixture, obstructs the dehydrogenative dimerization of the aromatic monocyclic compound. Accordingly, it is desirable that the reaction mixture contain no polar solvent as mentioned above.

In the process of the present invention, the oxalic acid cannot be replaced with another organic carboxylic acid, for example, acetic acid, formic acid and maleic acid, because these organic carboxylic acids not only cannot increase the percent selectivity to the resultant biphenyl compound but, also, tend to increase the yield of the undesirable by-product. This phenomenon will be illustrated by means of a comparison example hereinafter.

The dehydrogenative dimerization temperature may be in a range of from 25° to 300° C., preferably, from 100° to 200° C., still more preferably, from 120° to 160° C. This temperature is variable depending upon the type of the aromatic monocyclic compound and the partial pressure of the molecular oxygen in the reaction mixture. A dehydrogenative dimerization temperature higher than 300° C. might at times cause the percent selectivity to the resulting biphenyl compound to be reduced.

The molecular oxygen usable in the process of the present invention may be a pure oxygen gas. However, there is a danger of explosion when pure oxygen gas is used. Therefore, for the purpose of safety, it is preferable that pure oxygen gas be diluted with an inert gas, for instance, nitrogen gas and carbon dioxide gas. Especially, mixture gas consisting of 10 to 80% by volume of oxygen gas and the balance consisting of nitrogen gas, for example, air and a mixture of oxygen gas with air, is useful for the process of the present invention.

The time necessary for completing the hydrogenative dimerization reaction is variable depending on the composition temperature and pressure of the reaction mixture. Usually, the dehydrogenative dimerization reaction is carried out for from 1 to 100 hours.

In the process of the present invention, the product of the dehydrogenative dimerization reaction, that is, the resultant biphenyl compound, can be easily isolated from the reaction mixture by any conventional isolating methods, for example, distillation, extraction and recrystallization. The preferable isolation method is the distillation.

The process of the present invention is effective for producing the biphenyl compound with a higher percent selectivity thereof than that of the conventional processes. Also, the process of the present invention can be effected without the depositing of palladium black derived from the organic palladium salt. Even if a brown palladium complex is deposited from the reaction mixture during the dehydrogenative dimerization reaction, the reaction can be continued without any deficiency, because the brown palladium complex is highly active as a catalyst.

The features and advantages of the present invention will be further illustrated by the examples set forth below, which are merely illustrative and are not intended to limit the present invention is any way. In the examples, the percent conversion of the aromatic monocyclic compound into the corresponding biphenyl compound, and the percent selectivities of the biphenyl compound and the by-product are respectively determined in accordance with the following equations.

$$\text{Percent conversion of aromatic monocyclic compound} = \frac{X_1 - X_2}{X_1} \times 100$$

$$\text{Percent selectivity to biphenyl compound} = \frac{W}{X_1 - X_2} \times 100$$

and $$\text{Percent selectivity to by-product} = \frac{X_1 - X_2 - W}{X_1 - X_2} \times 100$$

wherein $X_1$ and $X_2$ respectively represent amounts (g) of the aromatic monocyclic compound in the reaction mixture before the start of the reaction and after the completion of the reaction and W represents an amount (g) of the resultant biphenyl compound and W represents an amount (g) of the resultant biphenyl compound.

EXAMPLES 1 THROUGH 5 AND COMPARISON EXAMPLE 1

An autoclave having a capacity of 270 ml, made of a SUS 32 stainless steel and being provided with an electomagnetic stirrer, was charged with 119 g of dimethyl orthophthalate, 0.6 millimoles of palladium acetate [Pd(O·CO·CH$_3$)$_2$] and 0.6 millimoles of oxalic acid [(COOH)$_2$]. A mixture gas consisting of 50% by volume of molecular oxygen and the balance consisting of nitrogen gas, was introduced into the autoclave until the inner pressure of the autoclave reached 50 kg/cm$^2$. The reaction mixture in the autoclave was heated at a temperature of 140° C. for 5 hours, so as to dehydrogenatively dimerize the dimethyl orthophthalate.

After the completion of the 5 hour reaction, the reaction mixture in the autoclave was cooled to a room temperature. The resultant reaction mixture was subjected to a distillation at a temperature to eliminate the unreacted dimethyl orthophthalate and to increase the concentration of the resultant biphenyl tetracarboxylic tetramethyl ester in the reaction mixture. The remaining reaction mixture was subjected to a gas chromatographic analysis, to determine the amounts of the biphenyl tetracarboxylic tetramethyl ester and the by-product having a high boiling point, that is, a pitch-like product. The percent conversion of the dimethyl orthophthalate into the biphenyl compound and the percent selectivities of the biphenyl compound and the by-product are shown in Table 1.

The resultant biphenyl tetracarboxylic tetramethyl ester consisted of a mixture of two biphenyl isomers, that is, 2,3,3',4'-biphenyl tetracarboxylic tetramethyl ester and 3,3',4,4'-biphenyl tetracarboxylic tetramethyl ester. The yields of the above-mentioned isomers are shown in Table 1. In each of the Examples 2 through 5, the same procedures as those described in Example 1 were carried out, except that the oxalic acid was used in the amount as indicated in Table 1. The results are shown in Table 1.

In Comparison Example 1, procedures identical to those described in Example 1 were carried out, except that no oxalic acid was used. The results are shown in Table 1.

TABLE 1

| | | | Dehydrogenative dimerization product | | | | | |
|---|---|---|---|---|---|---|---|---|
| | | | Biphenyl tetracarboxylic tetramethyl ester | | | | By-product | |
| Example No. | Amount of oxalic acid (m.mole) | Percent conversion of dimethyl orthophthalate (%) | Yield of 2,3,3',4'-substituted biphenyl isomer (g) | Yield of 3,3',4,4'-substituted biphenyl isomer (g) | Percent selectivity (%) | Percent yield (%) | Yield (g) | Percent selectivity (%) |
| Example 1 | 0.6 | 9.6 | 3.37 | 4.87 | 73.8 | 7.1 | 2.92 | 26.2 |
| Example 2 | 0.3 | 11.2 | 3.79 | 5.69 | 73.3 | 8.2 | 3.46 | 26.7 |
| Example 3 | 1.2 | 7.9 | 2.87 | 4.34 | 77.4 | 6.1 | 2.11 | 22.6 |
| Example 4 | 2.0 | 6.4 | 2.25 | 3.58 | 79.1 | 5.1 | 1.54 | 20.9 |
| Example 5 | 3.0 | 4.9 | 1.71 | 2.51 | 75.7 | 3.7 | 1.35 | 24.3 |
| Comparison Example 1 | 0 | 7.7 | 2.86 | 3.04 | 66.4 | 5.1 | 2.98 | 33.6 |

EXAMPLES 6 THROUGH 12 AND COMPARISON EXAMPLE 2

In each of Examples 6 through 9, the same procedures as those described in Example 1 were carried out, except that the oxalic acid was used in the amount as indicated in Table 2 and 0.6 millimoles of acetylacetone were used in addition to the palladium acetate. The results are shown in Table 2.

In Comparison Example 2, the same procedures as those described in Example 6 were carried out, except that no oxalic acid was used.

In each of Examples 10 through 12, the same procedures as those described in Example 1 were effected, except that the palladium acetate and the oxalic acid were used respectively in the amounts as indicated in Table 2.

TABLE 2

| | | | | | Dehydrogenative dimerization product | | | | |
|---|---|---|---|---|---|---|---|---|---|
| | | | | | Biphenyl tetracarboxylic tetramethyl ester | | | | By-product |
| Example No. | Amount of palladium acetate (m.mole) | Amount of oxalic acid (m.mole) | Amount of acetylacetone (m.mole) | Percent conversion of dimethyl orthophthalate | Yield of 2,3,3',4'-substituted biphenyl isomer (g) | Yield of 3,3',4,4'-substituted biphenyl isomer (g) | Percent selectivity (%) | Percent Yield (%) | Yield (g) | Percent selectivity (%) |
| Example 6 | 0.6 | 0.6 | 0.6 | 10.3 | 3.84 | 5.27 | 75.4 | 7.8 | 2.98 | 24.6 |
| Example 7 | 0.6 | 1.2 | 0.6 | 9.9 | 3.69 | 5.17 | 76.7 | 7.6 | 2.69 | 23.3 |
| Example 8 | 0.6 | 2.0 | 0.6 | 9.9 | 3.40 | 4.77 | 71.9 | 7.1 | 3.19 | 28.1 |
| Example 9 | 0.6 | 10.0 | 0.6 | 7.6 | 3.03 | 3.52 | 71.3 | 5.4 | 2.63 | 28.6 |
| Comparison Example 2 | 0.6 | 0 | 0.6 | 11.7 | 4.56 | 4.58 | 66.8 | 7.8 | 4.53 | 32.2 |
| Example 10 | 0.3 | 0.6 | 0 | 3.3 | 1.14 | 1.69 | 76.1 | 2.5 | 0.89 | 23.9 |
| Example 11 | 1.2 | 2.4 | 0 | 14.7 | 5.12 | 7.42 | 73.4 | 10.9 | 4.55 | 26.6 |
| Example 12 | 1.8 | 3.6 | 0 | 17.3 | 5.69 | 8.56 | 74.4 | 12.9 | 5.00 | 25.6 |

EXAMPLE 13

The same procedures as those mentioned in Example 3 were carried out, except that the oxalic acid [(COOH)$_2$] was replaced with oxalic acid dihydrate

[(COOH)$_2$·2H$_2$O]. The dimethyl orthophthalate was converted into the biphenyl tetracarboxylic tetramethyl ester at a percent conversion of 7.4%. The yields of the 2,3,3'4'-substituted biphenyl isomer and the 3,3',4,4'-substituted biphenyl isomer were respectively 2.59 g and 3.80 g. The yield of the by-product was 2.18 g. The percent selectivity to and the percent yield of the sum of the 2,3,3',4'- and 3,3',4,4'-substituted biphenyl isomer mixture were 74.5% by weight and 5.5% by weight, respectively. Also, the percent selectivity to the by-product was 25.4% by weight.

EXAMPLES 14 THROUGH 16

In each of the Examples 14 through 16, procedures identical to those mentioned in Example 3 were carried out, except that the initial pressure and temperature of the dehydrogenative dimerization reaction were changed to the values as indicated in Table 3, respectively. The results are shown in Table 3.

TABLE 3

| | | | | Item | | | | | |
|---|---|---|---|---|---|---|---|---|---|
| | | | | Dehydrogenative dimerization product | | | | | |
| | | | | Biphenyl tetracarboxylic tetramethyl ester | | | | By-product | |
| Example No. | Temperature (°C.) | Pressure (kg/cm$^2$) | Percent conversion of dimethyl orthophthalate (%) | Yield of 2,3,3',4'-substituted biphenyl isomer (g) | Yield of 3,3',4,4'-substituted biphenyl isomer (g) | Percent selectivity (%) | Percent yield (%) | Yield (g) | Percent selectivity (%) |
| Example 14 | 135 | 50 | 4.9 | 1.79 | 2.76 | 80.1 | 3.9 | 1.09 | 19.3 |
| Example 15 | 145 | 50 | 11.4 | 4.19 | 5.26 | 73.3 | 8.4 | 3.43 | 26.6 |
| Example 16 | 140 | 20 | 6.0 | 2.47 | 3.12 | 81.2 | 4.9 | 1.29 | 18.8 |

EXAMPLE 17

Procedures identical to those mentioned in Example 1 were carried out, except that 87.4 g of benzene were used for the dimethyl orthophthalate and the oxalic acid was used in an amount of 1.2 millimoles. The results were as follows.

| | |
|---|---|
| Percent conversion of benzene | = 0.63% |
| Yield of the resultant biphenyl | = 0.22 g |
| Yield of the by-product | = 0.09 g |
| Percent selectivity to the resultant biphenyl | = 71% by weight |
| Percent yield of the biphenyl | = 0.26% by weight |
| Percent selectivity to the by-product | = 29% by weight |

COMPARISON EXAMPLE 3

The same procedures as those described in Example 17 were carried out, except that no oxalic acid was contained in the reaction mixture. The results were as follows.

| | |
|---|---|
| Percent conversion of benzene | = 0.57% |
| Yield of the resultant biphenyl | = 0.29 g |
| Yield of the by-product | = 0.19 g |
| Percent selectivity to the biphenyl | = 61% by weight |
| Percent yield of the biphenyl | = 0.35% by weight |
| Percent selectivity to the by-product | = 39% by weight |

EXAMPLE 18

The same procedures as those mentioned in Example 1 were carried out, except that 61.4 g of o-xylene were used for the dimethyl orthophthalate, and the palladium acetate and the oxalic acid were each used in an amount of 0.42 millimoles. The resultant tetramethyl biphenyl was a mixture of 2,3,3',4'-tetramethyl biphenyl and 3,3',4,4'-tetramethyl biphenyl. The results were as follows.

| | |
|---|---|
| Percent conversion of o-xylene | = 12.0% |
| Yield of 2,3,3',4'-isomer | = 0.65 g |
| Yield of 3,3',4,4'-isomer | = 2.54 g |
| Yield of the by-product | = 4.41 g |
| Percent selectivity to the resultant tetramethyl biphenyl mixture | = 42% by weight |
| Percent Yield of the tetramethyl biphenyl mixture | = 5.4% by weight |
| Percent selectivity to the by-product | = 58% by weight |

COMPARISON EXAMPLE 4

The same procedures as those mentioned in Example 18 were carried out, except that no oxalic acid was used. The results were as follows.

| | |
|---|---|
| Percent conversion of o-xylene | = 20% |
| Yield of 2,3,3',4'-tetramethyl biphenyl | = 1.23 g |
| Yield of 3,3',4,4'-tetramethyl biphenyl | = 2.81 g |
| Yield of the by-product | = 8.42 g |
| Percent selectivity to the tetramethyl biphenyl mixture | = 32% by weight |
| Percent yield of the tetramethyl biphenyl mixture | = 6.4% by weight |
| Percent selectivity to the by-product | = 68% by weight |

COMPARISON EXAMPLE 5

The same procedures as described in Example 1 were carried out, except that 0.6 millimoles of formic acid were used for the oxalic acid. The results were as follows.

| | |
|---|---|
| Percent conversion of dimethyl orthophthalate | = 8.3% |
| Yield of 2,3,3',4'-biphenyl tetracarboxylic tetramethyl ester | = 2.84 g |
| Yield of 3,3',4,4'-biphenyl tetracarboxylic tetramethyl ester | = 2.81 g |
| Yield of the by-product | = 4.08 g |
| Percent selectivity to the resultant biphenyl compound mixture | = 58.1% by weight |
| Percent yield of the resultant biphenyl compound mixture | = 4.9% by weight |
| Percent selectivity to the by-product | = 41.9% by weight |

COMPARATIVE EXAMPLE 6

The same procedures as described in Example 1 were carried out, except that 1.2 millimoles of acetic acid were used for the oxalic acid. The results were as follows.

| | |
|---|---|
| Percent conversion of dimethyl | = 9.4% |
| Yield of 2,3,3',4'-biphenyl tetracarboxylic tetramethyl ester | = 3.33 g |
| Yield of 3,3',4,4'-biphenyl tetracarboxylic tetramethyl ester | =0 3.00 g |
| Yield of the by-product | = 4.59 g |
| Percent selectivity to the resultant biphenyl compound mixture | = 58.0% by weight |
| Percent yield of the biphenyl compound mixture | = 5.5% by weight |
| Percent selectivity to the by-product | = 42.0% by weight |

EXAMPLE 19

Procedures the same as those mentioned in Example 1 were carried out, except that 86.2 g of toluene were used for the dimethyl orthophthalate, 1.0 millimole of palladium benzoate were used for the palladium acetate, and the oxalic acid was used in an amount of 1.0 millimole. The resultant bitolyl product was a mixture of 2,2'-, 2,3'-, 2,4'-, 3,3'-, 3,4'- and 4,4'-dimethyl biphenyls. The results were as follows.

| | |
|---|---|
| Percent conversion of toluene | = 9.4% |
| Yield of the resultant biphenyl compound mixture | = 5.28 g |
| Yield of the by-product | = 2.84 g |
| Percent selectivity to the biphenyl compound mixture | = 65% by weight |
| Percent yield of the biphenyl compound mixture | = 6.1% by weight |
| Percent selectivity to the by-product | = 35% by weight |

COMPARISON EXAMPLE 7

The same procedures as those described in Example 19 were carried out, except that no oxalic acid was used. The results were as follows.

| | |
|---|---|
| Percent conversion of toluene | = 11.8% |
| Yield of the biphenyl compound mixture | = 5.63 g |
| Yield of the by-product | = 4.51 g |
| Percent selectivity to the biphenyl compound mixture | = 55.5% by weight |
| Percent yield of the biphenyl compound mixture | = 6.5% by weight |
| Percent selectivity to the by-product | = 44.5% by weight |

What we claim is:

1. A process for producing a biphenyl compound, comprising dehydrogenatively dimerizing an aromatic monocyclic compound selected from the group consisting of benzene and substituted benzene compounds having 1 to 4 substituents attached to the benzene ring thereof, with molecular oxygen in the presence of oxalic acid together with a catalyst comprising at least one organic palladium salt, under a pressurized condition, and, isolating the resulting biphenyl compound from the reaction mixture.

2. A process as claimed in claim 1, wherein the number of the substituents attached to the benzene ring is 1 or 2.

3. A process as claimed in claim 1, wherein said substituent is selected from the group consisting of unsubstituted and substituted alkyl radicals having 1 to 5 carbon atoms, alkoxycarbonyl radicals having 1 to 5 carbon atoms, alkoxy radicals having 1 to 5 carbon atoms, nitro radical and halogen atoms.

4. A process as claimed in claim 1, wherein said organic palladium salt is selected from the group consisting of palladium salts of aliphatic carboxylic acids having 1 to 5 carbon atoms and aromatic carboxylic acids, and palladium acetylacetonate.

5. A process as claimed in claim 1, wherein the amount of said organic palladium salt is in a range of from 0.01 to 100 millimoles per mole of said aromatic compound.

6. A process as claimed in claim 1, wherein the amount of said oxalic acid is in a range of from 0.05 to 50 moles per mole of said organic palladium salt.

7. A process as claimed in claim 1, wherein said pressure is in a range of from 4 to 400 kg/cm$^2$.

8. A process as claimed in claim 1, wherein said molecular oxygen has a partical pressure of from 2 to 300 kg/cm$^2$.

9. A process as claimed in claim 1, wherein said dehydrogenative dimerization is carried out at a temperature of from 25° to 300° C.

10. A process as claimed in claim 1, wherein said molecular oxygen is present in the state of a pure oxygen gas or a mixture of pure oxygen gas with an inert gas.

11. A process as claimed in claim 1, wherein said isolation of said resultant biphenyl compound is carried out by means of distillation.

* * * * *